United States Patent

Kleiner et al.

[11] 4,001,352
[45] Jan. 4, 1977

[54] PROCESS FOR THE PREPARATION OF ETHANE-1,2-DIPHOSPHINIC ACID DIESTERS

[75] Inventors: Hans-Jerg Kleiner, Bad Soden, Taunus; Walter Rupp, Schneidhain, Taunus, both of Germany

[73] Assignee: Hoechst Aktiengesellschaft, Frankfurt am Main, Germany

[22] Filed: Apr. 25, 1975

[21] Appl. No.: 571,769

Related U.S. Application Data

[63] Continuation of Ser. No. 434,030, Jan. 17, 1974, abandoned.

[30] Foreign Application Priority Data

Jan. 19, 1973 Germany .......................... 2302523

[52] U.S. Cl. ............................ 260/970; 204/158 R.
[51] Int. Cl.² ......................................... C07F 9/40
[58] Field of Search ........................ 260/970, 932; 204/158 R

[56] References Cited

UNITED STATES PATENTS

| | | | |
|---|---|---|---|
| 2,957,931 | 10/1960 | Hamilton et al. | 260/970 X |
| 3,812,222 | 5/1974 | Kleiner et al. | 260/970 |

*Primary Examiner*—Richard L. Raymond
*Attorney, Agent, or Firm*—Curtis, Morris & Safford

[57] ABSTRACT

A process for the preparation of ethane-1,2,-diphosphinic acid diesters of the formula

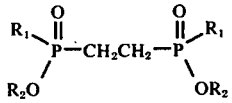

I where $R_1$ represents alkyl, phenyl and/or phenalkyl groups having from 1 to 18 carbon atoms and $R_2$ alkyl groups having from 1 to 18 carbon atoms, which may be optionally substituted by halogen atoms, which comprises reacting phosphonous acid esters of the formula

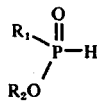

II where $R_1$ and $R_2$ are as define above, with acetylene in the presence of catalytic amounts of radical-forming agents and/or with UV irradiation.

5 Claims, No Drawings

PROCESS FOR THE PREPARATION OF ETHANE-1,2-DIPHOSPHINIC ACID DIESTERS

This is a continuation of application Ser. No. 434,030 filed Jan. 17, 1974, now abandoned.

The present invention relates to a process for the preparation of ethane-1,2-diphosphinic acid diesters.

Ethane-1,2-diphosphinic acid diesters are already known. They may be obtained with good yields from phosphonous acid disters and 1,2-dibromo-ethane by means of the Arbuzow reaction (P. Mastalerz, Roczniki Chem. 33, 985 (1959); Roczniki Chem. 38, 61 (1964); K. Issleib et al. B 101, 2197 (1968); T. Bratkowski et al., Roczniki Chem. 41, 471 (1967)). These diphosphinic acid diesters may also be obtained with an about 40% yield according to the Michaelis-Becker reaction from the sodium salts of the phosphonous acid monoesters which are more easily prepared on a large scale than the phosphonous acid diesters (V.S. Abramov et al., Z. obsc. Chim. 38, 1794 (1968)).

It has now been found that ethane-1,2-diphosphinic acid diesters of the formula

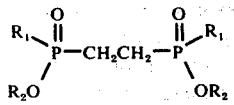

where $R_1$ represents alkyl, phenyl and/or phenalkyl groups having from 1 to 18 carbon atoms and $R_2$ alkyl groups having from 1 to 18 carbon atoms, which may be optionally substituted by halogen atoms, preferably chlorine, can be prepared with good yields by reacting phosphonous acid esters of the formula

where $R_1$ and $R_2$ are as defined above, with acetylene in the presence of catalytic amounts of radical-forming agents and/or with UV irradiation.

The phosphonous acid monoesters used as starting materials may be easily prepared according to known processes. As compounds of formula II, there may be used especially methane-phosphonous acid methyl, ethyl, propyl, n-butyl or isobutyl ester, methane-phosphonous acid 2-chloroethyl ester, ethane-phosphonous acid dodecyl ester, propane-phosphonous acid hexadecyl ester, benzene-phosphonous acid isobutyl ester, ethylbenzene-phosphonous acid isobutyl ester, benzyl-phosphonous acid isobutyl ester, phenethyl-phosphonous acid isobutyl ester, naphthalene-phosphonous acid isobutyl ester. Preferred compounds of formula II are those where $R_1$ is methyl or ethyl, and $R_2$ is alkyl having from 1 to 4 carbon atoms. The reaction is carried out at a temperature of from about 50° to 230° C, preferably from about 90° to 200° C, particularly from 130° to 160° C. The reaction is exothermal. When using UV light, reaction temperature of from about 140° to 230° C, preferably from 170° to 200° C, are required. The reaction is preferably carried out in the presence of inert gases, among which above all argon or nitrogen, but also carbon dioxide are suitable.

The radical-forming agents are used in catalytic amounts of from 0.05 to about 5 mole %, preferably from about 0.1 to 1 mole %, relative to the compound of formula II. They are advantageously dissolved in part of the phosphonous acid ester, optionally with the aid of inert solvents, and they are added slowly within the course of the reaction.

Suitable radical-forming agents are for example: ditert.-butylperoxide, tert.-butylperoxy-benzoate, 2,5-dimethylhexane-bis-2,5-(peroxybenzoate), tert.-butyl-hydroxyperoxide, dicumylperoxide, azo-bis-isobutanoldiacetate, azo-bis-isobutyronitrile, tert.-butylperoxy-ethane-nitrile-(2), tert.-butylperoxy-ethane-sulfonic acid n-butyl ester, dibenzoylperoxide, tert.-butyl-peroxy-pivalate. The radical-forming agents are chosen in view to the reaction temperature, in which temperature range the radical-forming agents should have a half decay period of from a few minutes to some seconds.

The reaction may be carried out in the presence of inert solvents. Examples are alcohols, esters and hydrocarbons, especially also compounds of formula I. Preferably, the reaction proceeds without solvents. Small amounts of the alcohols used for the preparation of the phosphonous acid esters, for example isobutanol, which are present in the reaction when crude non-purified phosphonous acid esters are employed, thus do not cause any troubles. This means that the reaction conditions are simplified.

The reaction in accordance with the present invention is carried out advantageously in the following manner: first, the phosphonous acid esters are heated to the desired reaction temperature under atmospheric pressure, preferably with exclusion of atmospheric oxygen. With vigorous atitation or intermixing, acetylene is then introduced to an extent which ensures its addition to the ester, while the catalyst solution is simultaneously fed in. Of course, the reaction may also be carried out under elevated pressure. It is also possible to introduce a phosphonic acid ester prepared in a first batch as dissolving intermediary into the reaction vessel and then to feed in the phosphonous acid ester mixed with the catalyst, while acetylene is introduced. This operation mode may also be used in order to make the process continuous; the phosphonic acid ester being taken off to that extent to which it is formed.

The addition of the acetylene to the phosphonous acid esters proceeds easily and nearly completely. Excesses above the stoichiometric amounts may be used, preferably up to 10%, but generally, about stoichiometric amounts are sufficient. By a suitable reaction control especially in continuous processes - acetylene and phosphonous acid ester in a counter-current - it is possible to react also non-consumed acetylene. Depending on the reaction temperature and the course of the reaction, the reaction times are from about ½ to 10 hours; a continuous operation requiring of course less reaction time.

The phosphinic acid esters are obtained with high yields. It is surprising to observe that practically no telomers and polymers are formed, although vinyl-phosphinic acid esters must be supposed to be obtained as intermediate products.

The crude ethane-1,2-diphosphinic acid diesters may be purified according to known methods by distillation or crystallization. They may be used as extraction agents for metal salts from acidic solutions. The long-chain esters have plastifying properties for plastics.

Furthermore, the compounds of formula I are especially interesting as intermediate products for the preparation of ethane-1,2-diphosphinic acids easily obtained from the above compounds with excellent purity degrees and yields by saponification or acid splitting according to known methods. The ethane-1,2-diphosphinic acids may be used for the preparation of flame-retarding oligomer or polymer esters according to German Offenlegungsschriften Nos. 2,236,036, 2,236,037, 2,236,038 and 2,236,039. Furthermore, ethane-1,2-diphosphinic acids may be employed for the preparation of flame repellent or flameproof polyurethanes (Swiss Patent No. 437,784). The alkali metal salts of such phosphinic acids may also be used for the flame repellent finishing of polyalkylene-terephthalates according to German Patent application No. P 22 52 258.3.

The following Examples illustrate the invention.

EXAMPLE 1

1.7 kg of methane-phosphonous acid isobutyl ester are heated to 190° C under a nitrogen atmosphere. Subsequently, acetylene is fed in for 5 hours with vigorous agitation, while a mixture of 100 g of methane-phosphonous acid isobutyl ester and 9 g of di-tert.-butyl-peroxide are added dropwise. After complete reaction, the reaction mixture is cooled to 90° C and partially distilled with reduced pressure, finally at 1–2 torrs, at a distillation temperature of up to 130° – 140° C. The 1.885 kg of distillation residue consist of 95% ethane-1,2-di-(methylphosphinic acid isobutyl ester), corresponding to a yield of 95.5%, relative to a 100% product. Purification may be carried out by distillation at 2 torrs and a distillation temperature of 198° C. The melting point of the product after distillation is 106° C.

EXAMPLE 2

2.6 kg of 92% methane-phosphonous acid isobutyl ester are heated to 150° C under a nitrogen atmosphere. Subsequently, acetylene is fed in for 6 hours with vigorous agitation, while a mixture of 400 g of 92% methane-phosphonous acid isobutyl ester and 20 g of azo-bis-isobutyronitrile is added dropwise. Since this reaction is exothermal, temporary cooling is necessary during the reaction period. The work-up is as indicated in Example 1. 2.88 kg of 94% ethane-1,2-di-(methylphosphinic acid isobutyl ester) are obtained as residue, which corresponds to a yield of 89%.

EXAMPLE 3

2.6 kg of 92% methane-phosphonous acid isobutyl ester are heated to 80° C under a nitrogen atmosphere. Subsequently, acetylene is introduced with vigorous agitation, while a mixture of 400 g of 92% methane-phosphonous acid isobutyl ester and 27 g of tert.-butyl-peroxypivalate is added dropwise. The temperature is slowly raised to 120°-130° C, which causes a rapid increase of the acetylene absorption. Temporary cooling is necessary, because the reaction is exothermal. After 4 hours, the reaction mixture is distilled. 2.71 kg of ethane-1,2-di-(methylphosphinic acid isobutyl ester) are obtained, which corresponds to a yield of 89%.

EXAMPLE 4 a. Preparation of ethane-1,2-di-(methylphosphinic acid isobutyl ester)

2 kg of a mixture of 75 weight % of methyne-phosphonous acid isobutyl ester and 25 weight % of isobutanol are heated to 150° C under a nitrogen blanket. Subsequently, acetylene is fed in with vigorous agitation, while a mixture of 370 g of the above mixture and 16.5 g of tert.-butyl-peroxybenzoate is added dropwise. About 95 g of catalyst solution and from 30 to 40 l of acetylene are added per hour. After a work-up according to Example 1, 1.99 kg of 93% ethane-1,2-di-(methyl-phosphinic acid isobutyl ester) are obtained, which corresponds to a yield of 95%.

b. Preparation of ethane-1,2-di-(methylphosphinic acid)

In a flask provided with agitator, descending condenser, receiver and subsequent deep-freezer trap, 1.85 kg of 93% ethane-1,2-di-(methylphosphinic acid isobutyl ester) are heated to 160° C, and dry hydrogen chloride is fed in with vigorous agitation. After a short time, isobutyl chloride begins to distil off. As a by-product, a small amount of isobutene is formed which is condensed in the deep-freezer trap. Within 5 hours, the temperature is raised to 200° C, which causes the complete absorption of the hydrogen chloride even when it is fed in in large amounts. When the reaction is complete, a total of about 830 g of isobutyl chloride and 150 g of isobutene have split off. In the flask, there are about 1.1 kg of molten crude ethane-1,2-di-(methylphosphinic acid) which are poured off and crushed after solidification. Subsequently, the acid is boiled in 2.3 l of iso-propanol, until it is obtained in a pulverized crystal form. After cooling and suction-filtration, 0.995 kg of ethane-1,2-di-(methylphosphinic acid) is obtained, having a melting point of 190° – 192° C, and of 194° – 196° C after recrystallization from glacial acetic acid. This corresponds to a yield of 92.5%.

EXAMPLE 5

600 g of a mixture of 75% of methane-phosphonous acid isobutyl ester and 25% of isobutanol are heated to 180° C under a nitrogen atmosphere. Subsequently, acetylene is fed in with vigorous agitation and with simultaneous UV irradiation for 7 hours by means of a mercury lamp. During the reaction, the temperature is raised to 200° C. In a cooled receiver connected to the reaction vessel, isobutanol which is distilling off may be collected. After complete reaction, distillation is carried out. 400 g of ethane-1,2-di-(methylphosphinic acid isobutyl ester) are obtained, which corresponds to a yield of 81%.

EXAMPLE 6

431 g of benzene-phosphonous acid isobutyl ester are heated to 180° – 190° C under a nitrogen atmosphere. Subsequently, acetylene is fed in with vigorous agitation, while a mixture of 48 g of benzene-phosphonous acid acid isobutyl ester and 4 g of di-tert.-butylperoxide is added dropwise. After distillation at 0.5 torr and an internal temperature of 115° C, 433 g of ethane-1,2-di-(phenylphosphinic acid isobutyl ester) are obtained as residue, which crystallize on cooling. The amount corresponds to a yield of 94%.

We claim:

1. In a process for the preparation of an ethane-1,2-diphosphonic acid diester of the formula

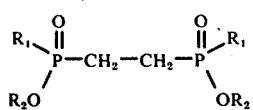

wherein $R_1$ represents an alkyl, phenyl and/or phenylalkyl group having from 1 to 18 carbon atoms and $R_2$ is an alkyl group or a halogen substituted alkyl group having from 1 to 18 carbon atoms, by reacting with acetylene a phosphonous acid ester of the formula

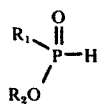

wherein $R_1$ and $R_2$ are as defined above, at a temperature of from 50° to 230° C in the presence of a catalytic amount of a radical-forming agent, the improvement which comprises first heating said phosphonous acid ester to the desired reaction temperature under atmospheric pressure with the exclusion of atmospheric oxygen and then introducing acetylene and simultaneously slowly adding the radical-forming agent dissolved in said phosphonous acid ester.

2. A process as claimed in claim 1, wherein the reaction is carried out in the presence of a solvent.

3. A process as claimed in claim 1, wherein the reaction is carried out in the presence of isobutanol as solvent, when $R_2$ is isobutyl.

4. A process as claimed in claim 1, wherein the reaction is carried out in the presence of tert.-butyl-peroxybenzoate in a temperature range of from 130° to 160° C.

5. A process as claimed in claim 1, wherein the first heating is carried out under the protective gas atmosphere of nitrogen.

* * * * *